(12) United States Patent
Perron et al.

(10) Patent No.: US 8,517,915 B2
(45) Date of Patent: Aug. 27, 2013

(54) REMOTELY ADJUSTABLE GASTRIC BANDING SYSTEM

(75) Inventors: Christian Y. Perron, Goleta, CA (US); Sean Snow, Carpinteria, CA (US); Mike Augarten, Goleta, CA (US); Robert Hoyt, Jr., Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 478 days.

(21) Appl. No.: 12/813,355

(22) Filed: Jun. 10, 2010

(65) Prior Publication Data

US 2011/0306824 A1 Dec. 15, 2011

(51) Int. Cl.
*A61F 2/04* (2006.01)

(52) U.S. Cl.
USPC .............. 600/37; 606/201; 606/151; 604/909

(58) Field of Classification Search
USPC ............... 600/29–31, 37; 606/151, 157, 201, 606/202; 604/909
See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

(Continued)

*Primary Examiner* — Charles A Marmor, II
*Assistant Examiner* — Laura Fajardo
(74) *Attorney, Agent, or Firm* — Stephen Donovan; Debra Condino

(57) ABSTRACT

An implantable system comprises a housing that includes a flexible reservoir. The flexible reservoir is coupled to an inflatable portion of a gastric band via a fluid inlet/outlet. The flexible reservoir contains a fluid and has an expanded configuration and a contracted configuration. An access port may be coupled to the flexible reservoir and/or the gastric band to facilitate filling and draining the reservoir and/or the gastric band. A movable wall is slidably positioned around the flexible reservoir to move the flexible reservoir between the expanded configuration and the contracted configuration to move the fluid into and out of the inflatable portion of the gastric band. A driving mechanism is positioned around the movable wall and is capable of changing the size of the movable wall to compress or expand the flexible reservoir. A motor, coupled to the driving mechanism, may actuate the driving mechanism.

12 Claims, 9 Drawing Sheets

(56) References Cited

U.S. PATENT DOCUMENTS

| | | | |
|---|---|---|---|
| 3,667,081 A | 6/1972 | Burger | |
| 3,840,018 A | 10/1974 | Heifetz | |
| 3,955,834 A | 5/1976 | Ahlrot | |
| 4,053,176 A | 10/1977 | Hilbush | |
| 4,118,805 A | 10/1978 | Reimels | |
| 4,133,315 A | 1/1979 | Berman et al. | |
| 4,157,713 A | 6/1979 | Clarey | |
| 4,176,412 A | 12/1979 | Peterson | |
| 4,236,521 A | 12/1980 | Lauterjung | |
| 4,271,827 A | 6/1981 | Angelchik | |
| 4,299,012 A | 11/1981 | Oetiker | |
| 4,340,083 A | 7/1982 | Cummins | |
| 4,399,809 A | 8/1983 | Baro et al. | |
| 4,406,656 A | 9/1983 | Hattler et al. | |
| 4,408,597 A | 10/1983 | Tenney, Jr. et al. | |
| 4,417,567 A | 11/1983 | Trick | |
| 4,424,208 A | 1/1984 | Wallace et al. | |
| 4,442,153 A | 4/1984 | Meltsch | |
| 4,450,375 A | 5/1984 | Siegal | |
| 4,485,805 A | 12/1984 | Foster, Jr. | |
| 4,492,004 A | 1/1985 | Oetiker | |
| 4,551,862 A | 11/1985 | Haber | |
| 4,558,699 A | 12/1985 | Bashour | |
| 4,559,699 A | 12/1985 | Owen et al. | |
| 4,582,640 A | 4/1986 | Smestad et al. | |
| 4,582,865 A | 4/1986 | Balazs et al. | |
| 4,592,339 A | 6/1986 | Kuzmak et al. | |
| 4,592,355 A | 6/1986 | Antebi | |
| 4,601,713 A | 7/1986 | Fuqua | |
| 4,667,672 A | 5/1987 | Romanowski | |
| 4,671,351 A | 6/1987 | Rappe | |
| 4,693,695 A | 9/1987 | Cheng | |
| 4,694,827 A | 9/1987 | Weiner et al. | |
| 4,696,288 A | 9/1987 | Kuzmak et al. | |
| 4,708,140 A | 11/1987 | Baron | |
| 4,716,154 A | 12/1987 | Malson et al. | |
| 4,753,086 A | 6/1988 | Schmidt | |
| 4,760,837 A | 8/1988 | Petit | |
| 4,803,075 A | 2/1989 | Wallace et al. | |
| 4,881,939 A | 11/1989 | Newman | |
| 4,883,467 A | 11/1989 | Franetzki et al. | |
| 4,886,787 A | 12/1989 | De Belder et al. | |
| 4,896,787 A | 1/1990 | Delamour et al. | |
| 4,915,690 A | 4/1990 | Cone et al. | |
| 4,925,446 A | 5/1990 | Garay et al. | |
| 4,944,487 A | 7/1990 | Holtermann | |
| 4,944,659 A | 7/1990 | Labbe et al. | |
| 4,958,791 A | 9/1990 | Nakamura | |
| 4,969,899 A | 11/1990 | Cox, Jr. | |
| 4,994,019 A | 2/1991 | Fernandez et al. | |
| 5,041,094 A * | 8/1991 | Perego et al. | 604/143 |
| 5,045,060 A | 9/1991 | Melsky et al. | |
| 5,074,868 A | 12/1991 | Kuzmak | |
| 5,084,061 A | 1/1992 | Gau et al. | |
| 5,089,019 A | 2/1992 | Grandjean | |
| 5,091,171 A | 2/1992 | Yu et al. | |
| 5,116,652 A | 5/1992 | Alzner | |
| 5,120,313 A | 6/1992 | Elftman | |
| 5,143,724 A | 9/1992 | Leshchiner et al. | |
| 5,152,770 A | 10/1992 | Bengmark et al. | |
| 5,160,338 A | 11/1992 | Vincent | |
| 5,188,609 A | 2/1993 | Bayless et al. | |
| 5,224,494 A | 7/1993 | Enhorning | |
| 5,226,429 A | 7/1993 | Kuzmak | |
| 5,246,456 A | 9/1993 | Wilkinson | |
| 5,246,698 A | 9/1993 | Leshchiner et al. | |
| 5,259,399 A | 11/1993 | Brown | |
| 5,326,349 A | 7/1994 | Baraff | |
| 5,343,894 A | 9/1994 | Frisch et al. | |
| 5,356,883 A | 10/1994 | Kuo et al. | |
| 5,360,445 A | 11/1994 | Goldowsky | |
| 5,391,156 A | 2/1995 | Hildwein et al. | |
| 5,399,351 A | 3/1995 | Leshchiner et al. | |
| 5,449,363 A | 9/1995 | Brust et al. | |
| 5,449,368 A | 9/1995 | Kuzmak | |
| 5,458,568 A | 10/1995 | Racchini et al. | |
| 5,496,312 A | 3/1996 | Klicek | |
| 5,509,888 A | 4/1996 | Miller | |
| 5,531,716 A | 7/1996 | Luzio et al. | |
| 5,535,752 A | 7/1996 | Halperin et al. | |
| 5,554,113 A | 9/1996 | Novak et al. | |
| 5,562,714 A | 10/1996 | Grevious | |
| 5,601,604 A | 2/1997 | Vincent | |
| 5,607,418 A | 3/1997 | Arzbaecher | |
| 5,633,001 A | 5/1997 | Agerup | |
| 5,653,718 A | 8/1997 | Yoon | |
| 5,658,298 A | 8/1997 | Vincent et al. | |
| 5,676,162 A | 10/1997 | Larson, Jr. et al. | |
| 5,695,504 A | 12/1997 | Gifford, III et al. | |
| 5,704,893 A | 1/1998 | Timm | |
| 5,713,911 A | 2/1998 | Racenet et al. | |
| 5,733,257 A | 3/1998 | Sternby | |
| 5,748,200 A | 5/1998 | Funahashi | |
| 5,759,015 A | 6/1998 | Van Lintel et al. | |
| 5,766,232 A | 6/1998 | Grevious et al. | |
| 5,769,877 A | 6/1998 | Barreras, Sr. | |
| 5,785,295 A | 7/1998 | Tsai | |
| 5,807,311 A | 9/1998 | Palestrant | |
| 5,817,113 A | 10/1998 | Gifford, III et al. | |
| 5,827,529 A | 10/1998 | Ono et al. | |
| 5,833,698 A | 11/1998 | Hinchliffe et al. | |
| 5,861,014 A | 1/1999 | Familoni | |
| RE36,176 E | 3/1999 | Kuzmak | |
| 5,886,042 A | 3/1999 | Yu et al. | |
| 5,904,697 A | 5/1999 | Gifford, III et al. | |
| 5,910,149 A | 6/1999 | Kuzmak | |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 5,993,473 A | 11/1999 | Chan et al. | |
| 6,013,679 A | 1/2000 | Kuo et al. | |
| 6,024,340 A | 2/2000 | Lazarus et al. | |
| 6,024,704 A | 2/2000 | Meador et al. | |
| 6,042,345 A | 3/2000 | Bishop et al. | |
| 6,048,309 A | 4/2000 | Flom et al. | |
| 6,067,991 A | 5/2000 | Forsell | |
| 6,074,341 A | 6/2000 | Anderson et al. | |
| 6,074,378 A | 6/2000 | Mouri et al. | |
| 6,083,249 A | 7/2000 | Familoni | |
| 6,090,131 A | 7/2000 | Daley | |
| 6,102,922 A | 8/2000 | Jakobsson et al. | |
| 6,164,933 A | 12/2000 | Tani et al. | |
| 6,171,321 B1 | 1/2001 | Gifford, III et al. | |
| 6,193,734 B1 | 2/2001 | Bolduc et al. | |
| 6,203,523 B1 | 3/2001 | Haller et al. | |
| 6,210,345 B1 | 4/2001 | Van Brunt | |
| 6,210,347 B1 | 4/2001 | Forsell | |
| 6,221,024 B1 | 4/2001 | Miesel | |
| 6,224,857 B1 | 5/2001 | Romeo et al. | |
| 6,306,088 B1 | 10/2001 | Krausman et al. | |
| 6,327,503 B1 | 12/2001 | Familoni | |
| 6,371,965 B2 | 4/2002 | Gifford, III et al. | |
| 6,372,494 B1 | 4/2002 | Naughton et al. | |
| 6,383,218 B1 | 5/2002 | Sourdile et al. | |
| 6,383,219 B1 | 5/2002 | Telandro et al. | |
| 6,387,105 B1 | 5/2002 | Gifford, III et al. | |
| 6,417,750 B1 | 7/2002 | Sohn | |
| 6,418,934 B1 | 7/2002 | Chin | |
| 6,419,696 B1 | 7/2002 | Ortiz et al. | |
| 6,432,040 B1 | 8/2002 | Meah | |
| 6,439,539 B1 | 8/2002 | Powell | |
| 6,443,957 B1 | 9/2002 | Addis | |
| 6,443,965 B1 | 9/2002 | Gifford, III et al. | |
| 6,450,173 B1 | 9/2002 | Forsell | |
| 6,450,946 B1 | 9/2002 | Forsell | |
| 6,450,987 B1 | 9/2002 | Kramer | |
| 6,451,034 B1 | 9/2002 | Gifford, III et al. | |
| 6,453,907 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,454,785 B2 | 9/2002 | De Hoyos Garza | |
| 6,457,801 B1 | 10/2002 | Fish et al. | |

| | | | | | | |
|---|---|---|---|---|---|---|
| 6,460,543 B1 * | 10/2002 | Forsell ................... 128/898 | 7,351,198 B2 | 4/2008 | Byrum et al. |
| 6,461,293 B1 | 10/2002 | Forsell | 7,351,240 B2 | 4/2008 | Hassler, Jr. et al. |
| 6,463,935 B1 | 10/2002 | Forsell | 7,353,747 B2 | 4/2008 | Swayze et al. |
| 6,464,628 B1 | 10/2002 | Forsell | 7,364,542 B2 | 4/2008 | Jambor et al. |
| 6,470,892 B1 | 10/2002 | Forsell | 7,366,571 B2 | 4/2008 | Armstrong |
| 6,474,584 B2 | 11/2002 | Ekich | 7,367,340 B2 | 5/2008 | Nelson et al. |
| 6,475,136 B1 | 11/2002 | Forsell | 7,367,937 B2 | 5/2008 | Jambor et al. |
| 6,485,496 B1 | 11/2002 | Suyker et al. | 7,374,565 B2 | 5/2008 | Hassler, Jr. et al. |
| 6,491,704 B2 | 12/2002 | Gifford, III et al. | 7,390,294 B2 | 6/2008 | Hassler |
| 6,491,705 B2 | 12/2002 | Gifford, III et al. | 7,396,353 B2 | 7/2008 | Lorenzen et al. |
| 6,511,490 B2 | 1/2003 | Robert | 7,416,528 B2 | 8/2008 | Crawford et al. |
| 6,517,556 B1 | 2/2003 | Monassevitch | 7,457,668 B2 | 11/2008 | Cancel et al. |
| 6,527,701 B1 | 3/2003 | Sayet et al. | 7,481,763 B2 | 1/2009 | Hassler et al. |
| 6,547,801 B1 * | 4/2003 | Dargent et al. ............ 606/157 | 7,500,944 B2 | 3/2009 | Byrum et al. |
| 6,565,582 B2 | 5/2003 | Gifford, III et al. | 7,502,649 B2 | 3/2009 | Ben-Haim et al. |
| 6,579,301 B1 | 6/2003 | Bales et al. | 7,530,943 B2 | 5/2009 | Lechner |
| 6,601,604 B1 | 8/2003 | Cooper | 7,594,885 B2 | 9/2009 | Byrum |
| 6,615,084 B1 | 9/2003 | Cigaina | 7,599,743 B2 | 10/2009 | Hassler, Jr. et al. |
| 6,627,620 B1 | 9/2003 | Nielsen | 7,599,744 B2 | 10/2009 | Giordano et al. |
| 6,630,486 B1 | 10/2003 | Royer | 7,601,162 B2 | 10/2009 | Hassler, Jr. et al. |
| 6,632,239 B2 | 10/2003 | Snyder et al. | 7,615,001 B2 | 11/2009 | Jambor et al. |
| 6,646,628 B2 | 11/2003 | Shirochi et al. | 7,618,365 B2 | 11/2009 | Jambor et al. |
| 6,676,674 B1 | 1/2004 | Dudai | 7,658,196 B2 | 2/2010 | Ferreri et al. |
| 6,681,135 B1 | 1/2004 | Davis et al. | 7,670,279 B2 | 3/2010 | Gertner |
| 6,685,668 B1 | 2/2004 | Cho et al. | 7,699,770 B2 | 4/2010 | Hassler, Jr. et al. |
| 6,685,963 B1 | 2/2004 | Taupin et al. | 7,712,470 B2 | 5/2010 | Gertner |
| 6,691,047 B1 | 2/2004 | Fredericks | 7,727,141 B2 | 6/2010 | Hassler, Jr. et al. |
| 6,715,731 B1 | 4/2004 | Post et al. | 7,741,476 B2 | 6/2010 | Lebreton |
| 6,729,600 B2 | 5/2004 | Mattes et al. | 7,758,493 B2 | 7/2010 | Gingras |
| 6,754,527 B2 | 6/2004 | Stroebel et al. | 7,763,039 B2 | 7/2010 | Ortiz et al. |
| 6,767,924 B2 | 7/2004 | Yu et al. | 7,766,815 B2 | 8/2010 | Ortiz |
| 6,811,136 B2 | 11/2004 | Eberhardt et al. | 7,771,439 B2 | 8/2010 | Griffiths |
| 6,820,651 B2 | 11/2004 | Seuret et al. | 7,775,215 B2 | 8/2010 | Hassler, Jr. et al. |
| 6,834,201 B2 | 12/2004 | Gillies et al. | 7,775,966 B2 | 8/2010 | Dlugos et al. |
| 6,871,090 B1 | 3/2005 | He et al. | 7,775,967 B2 | 8/2010 | Gertner |
| 6,889,086 B2 | 5/2005 | Mass et al. | 7,794,386 B2 | 9/2010 | Brooks |
| 6,916,326 B2 | 7/2005 | Benchetrit | 7,811,298 B2 | 10/2010 | Birk |
| 6,921,819 B2 | 7/2005 | Piron et al. | 7,824,422 B2 | 11/2010 | Benchetrit |
| 6,924,273 B2 | 8/2005 | Pierce | 7,828,813 B2 | 11/2010 | Mouton |
| 6,940,467 B2 | 9/2005 | Fischer et al. | 7,832,407 B2 | 11/2010 | Gertner |
| 6,966,875 B1 | 11/2005 | Longobardi | 7,841,978 B2 | 11/2010 | Gertner |
| 7,017,583 B2 | 3/2006 | Forsell | 7,844,342 B2 | 11/2010 | Dlugos et al. |
| 7,017,883 B2 | 3/2006 | Bayer et al. | 7,862,502 B2 | 1/2011 | Pool et al. |
| 7,021,147 B1 | 4/2006 | Subramanian et al. | 7,879,068 B2 | 2/2011 | Dlugos et al. |
| 7,037,344 B2 | 5/2006 | Kagan et al. | 7,951,067 B2 | 5/2011 | Byrum et al. |
| 7,040,349 B2 | 5/2006 | Moler et al. | 2001/0011543 A1 | 8/2001 | Forsell |
| 7,048,519 B2 | 5/2006 | Fong et al. | 2002/0072780 A1 | 6/2002 | Foley |
| 7,054,690 B2 | 5/2006 | Imran | 2002/0091395 A1 | 7/2002 | Gabbay |
| 7,058,434 B2 | 6/2006 | Wang et al. | 2002/0095181 A1 | 7/2002 | Beyar |
| 7,060,080 B2 | 6/2006 | Bachmann | 2002/0098097 A1 | 7/2002 | Singh |
| 7,066,486 B2 | 6/2006 | Lee | 2002/0139208 A1 | 10/2002 | Yatskov |
| 7,118,526 B2 | 10/2006 | Egle | 2002/0183765 A1 | 12/2002 | Adams |
| 7,119,062 B1 | 10/2006 | Alvis et al. | 2002/0193679 A1 | 12/2002 | Malave et al. |
| 7,128,750 B1 | 10/2006 | Stergiopulos | 2002/0198548 A1 | 12/2002 | Robert |
| 7,144,400 B2 | 12/2006 | Byrum et al. | 2003/0014003 A1 | 1/2003 | Gertner |
| 7,172,607 B2 | 2/2007 | Hofle et al. | 2003/0019498 A1 | 1/2003 | Forsell |
| 7,177,693 B2 | 2/2007 | Starkebsum | 2003/0045775 A1 | 3/2003 | Forsell |
| 7,191,007 B2 | 3/2007 | Desai et al. | 2003/0045902 A1 | 3/2003 | Weadock |
| 7,198,250 B2 | 4/2007 | East | 2003/0055311 A1 | 3/2003 | Neukermans et al. |
| 7,204,821 B1 | 4/2007 | Clare et al. | 2003/0060873 A1 | 3/2003 | Gertner et al. |
| 7,206,637 B2 | 4/2007 | Salo | 2003/0066536 A1 | 4/2003 | Forsell |
| 7,223,239 B2 | 5/2007 | Schulze et al. | 2003/0073880 A1 | 4/2003 | Polsky et al. |
| 7,238,191 B2 | 7/2007 | Bachmann | 2003/0093157 A1 | 5/2003 | Caseres et al. |
| 7,240,607 B2 | 7/2007 | Fish | 2003/0100910 A1 | 5/2003 | Gifford, III et al. |
| 7,255,675 B2 | 8/2007 | Gertner et al. | 2003/0120288 A1 | 6/2003 | Benchetrit |
| 7,263,405 B2 | 8/2007 | Boveja et al. | 2003/0148995 A1 | 8/2003 | Piron et al. |
| 7,282,023 B2 | 10/2007 | Frering | 2003/0158564 A1 | 8/2003 | Benchetrit |
| 7,284,966 B2 | 10/2007 | Xu et al. | 2003/0158569 A1 | 8/2003 | Wazne |
| 7,288,064 B2 | 10/2007 | Boustani et al. | 2003/0181890 A1 | 9/2003 | Schulze et al. |
| 7,297,103 B2 | 11/2007 | Jarsaillon et al. | 2003/0181917 A1 | 9/2003 | Gertner |
| 7,299,082 B2 | 11/2007 | Feldman et al. | 2003/0191433 A1 | 10/2003 | Prentiss |
| 7,310,557 B2 | 12/2007 | Maschino et al. | 2003/0208212 A1 | 11/2003 | Cigaina |
| 7,311,503 B2 | 12/2007 | Van Lintel et al. | 2004/0000843 A1 | 1/2004 | East |
| 7,311,716 B2 | 12/2007 | Byrum | 2004/0044332 A1 | 3/2004 | Stergiopulos |
| 7,311,717 B2 | 12/2007 | Egle | 2004/0049209 A1 | 3/2004 | Benchetrit |
| 7,314,443 B2 | 1/2008 | Jordan et al. | 2004/0059393 A1 | 3/2004 | Policker et al. |
| 7,314,636 B2 | 1/2008 | Caseres et al. | 2004/0068847 A1 | 4/2004 | Belisle et al. |
| 7,338,433 B2 | 3/2008 | Coe | 2004/0106899 A1 | 6/2004 | McMichael et al. |
| 7,340,306 B2 | 3/2008 | Barrett et al. | 2004/0133219 A1 | 7/2004 | Forsell |

| | | | | | | |
|---|---|---|---|---|---|---|
| 2004/0147816 A1 | 7/2004 | Policker et al. | | 2006/0211912 A1 | 9/2006 | Dlugos et al. |
| 2004/0148034 A1 | 7/2004 | Kagan et al. | | 2006/0211913 A1 | 9/2006 | Dlugos et al. |
| 2004/0153106 A1 | 8/2004 | Dudai | | 2006/0211914 A1 | 9/2006 | Hassler, Jr. et al. |
| 2004/0162595 A1 | 8/2004 | Foley | | 2006/0212051 A1 | 9/2006 | Snyder et al. |
| 2004/0215159 A1 | 10/2004 | Forsell | | 2006/0212053 A1 | 9/2006 | Gertner |
| 2004/0230137 A1 | 11/2004 | Mouton | | 2006/0235448 A1 | 10/2006 | Roslin et al. |
| 2004/0254536 A1 | 12/2004 | Conlon et al. | | 2006/0246137 A1 | 11/2006 | Hermitte et al. |
| 2004/0254537 A1 | 12/2004 | Conlon et al. | | 2006/0247721 A1 | 11/2006 | Maschino et al. |
| 2004/0260319 A1 | 12/2004 | Egle | | 2006/0247722 A1 | 11/2006 | Maschino et al. |
| 2004/0267288 A1 | 12/2004 | Byrum et al. | | 2006/0247724 A1 | 11/2006 | Gerber et al. |
| 2004/0267291 A1 | 12/2004 | Byrum et al. | | 2006/0252982 A1 | 11/2006 | Hassler, Jr. et al. |
| 2004/0267292 A1 | 12/2004 | Byrum et al. | | 2006/0252983 A1 | 11/2006 | Lembo et al. |
| 2004/0267293 A1 | 12/2004 | Byrum et al. | | 2006/0257488 A1 | 11/2006 | Hubbard |
| 2004/0267377 A1 | 12/2004 | Egle | | 2006/0264699 A1 | 11/2006 | Gertner |
| 2005/0002984 A1 | 1/2005 | Byrum et al. | | 2006/0276812 A1 | 12/2006 | Hill et al. |
| 2005/0038484 A1 | 2/2005 | Knudson et al. | | 2006/0293627 A1 | 12/2006 | Byrum et al. |
| 2005/0038498 A1 | 2/2005 | Dubrow et al. | | 2007/0015954 A1 | 1/2007 | Dlugos |
| 2005/0055039 A1 | 3/2005 | Burnett et al. | | 2007/0015955 A1 | 1/2007 | Tsonton |
| 2005/0070934 A1 | 3/2005 | Tanaka et al. | | 2007/0015956 A1 | 1/2007 | Crawford et al. |
| 2005/0070937 A1 | 3/2005 | Jambor et al. | | 2007/0016231 A1 | 1/2007 | Jambor et al. |
| 2005/0100779 A1 | 5/2005 | Gertner | | 2007/0016262 A1 | 1/2007 | Gross et al. |
| 2005/0104457 A1 | 5/2005 | Jordan et al. | | 2007/0027356 A1 | 2/2007 | Ortiz |
| 2005/0119672 A1 | 6/2005 | Benchetrit | | 2007/0027358 A1 | 2/2007 | Gertner et al. |
| 2005/0119674 A1 | 6/2005 | Gingras | | 2007/0044655 A1 | 3/2007 | Fish |
| 2005/0131383 A1 | 6/2005 | Chen et al. | | 2007/0077292 A1 | 4/2007 | Pinsky |
| 2005/0131485 A1 | 6/2005 | Knudson et al. | | 2007/0078476 A1 | 4/2007 | Hull, Sr. et al. |
| 2005/0136122 A1 | 6/2005 | Sadozai et al. | | 2007/0125826 A1 | 6/2007 | Shelton |
| 2005/0142152 A1 | 6/2005 | Leshchiner et al. | | 2007/0156013 A1 | 7/2007 | Birk |
| 2005/0143765 A1 | 6/2005 | Bachmann et al. | | 2007/0167672 A1 | 7/2007 | Dlugos et al. |
| 2005/0143766 A1 | 6/2005 | Bachmann et al. | | 2007/0167982 A1 | 7/2007 | Gertner et al. |
| 2005/0154274 A1 | 7/2005 | Jarsaillon et al. | | 2007/0173685 A1 | 7/2007 | Jambor et al. |
| 2005/0171568 A1 | 8/2005 | Duffy | | 2007/0173888 A1 | 7/2007 | Gertner et al. |
| 2005/0183730 A1 | 8/2005 | Byrum | | 2007/0179335 A1 | 8/2007 | Gertner et al. |
| 2005/0192531 A1 | 9/2005 | Birk | | 2007/0185373 A1 | 8/2007 | Tsonton |
| 2005/0192601 A1 | 9/2005 | Demarais | | 2007/0185462 A1 | 8/2007 | Byrum |
| 2005/0192614 A1 | 9/2005 | Binmoeller | | 2007/0213836 A1 | 9/2007 | Paganon |
| 2005/0192629 A1 | 9/2005 | Saadat et al. | | 2007/0218083 A1 | 9/2007 | Brooks |
| 2005/0216042 A1 | 9/2005 | Gertner | | 2007/0232848 A1 | 10/2007 | Forsell |
| 2005/0226936 A1 | 10/2005 | Agerup | | 2007/0232849 A1 | 10/2007 | Gertner |
| 2005/0228415 A1 | 10/2005 | Gertner | | 2007/0233170 A1 | 10/2007 | Gertner |
| 2005/0228504 A1 | 10/2005 | Demarais | | 2007/0235083 A1 | 10/2007 | Dlugos |
| 2005/0240155 A1 | 10/2005 | Conlon | | 2007/0243227 A1 | 10/2007 | Gertner |
| 2005/0240156 A1 | 10/2005 | Conlon | | 2007/0250085 A1 | 10/2007 | Bachmann et al. |
| 2005/0240279 A1 | 10/2005 | Kagan et al. | | 2007/0250086 A1 | 10/2007 | Wiley et al. |
| 2005/0244288 A1 | 11/2005 | O'Neill | | 2007/0255335 A1 | 11/2007 | Herbert et al. |
| 2005/0250979 A1 | 11/2005 | Coe | | 2007/0255336 A1 | 11/2007 | Herbert et al. |
| 2005/0251181 A1 | 11/2005 | Bachmann | | 2007/0265598 A1 | 11/2007 | Karasik |
| 2005/0251182 A1 | 11/2005 | Bachmann | | 2007/0265645 A1* | 11/2007 | Birk et al. ..................... 606/157 |
| 2005/0267406 A1 | 12/2005 | Hassler, Jr. | | 2007/0265646 A1 | 11/2007 | McCoy et al. |
| 2005/0267500 A1 | 12/2005 | Hassler, Jr. et al. | | 2007/0293716 A1 | 12/2007 | Baker et al. |
| 2005/0267533 A1 | 12/2005 | Gertner | | 2007/0298005 A1 | 12/2007 | Thibault |
| 2005/0271729 A1 | 12/2005 | Wang | | 2008/0009680 A1 | 1/2008 | Hassler, Jr. |
| 2005/0277899 A1 | 12/2005 | Conlon et al. | | 2008/0015406 A1 | 1/2008 | Dlugos et al. |
| 2005/0283041 A1 | 12/2005 | Egle | | 2008/0015501 A1 | 1/2008 | Gertner |
| 2005/0288739 A1 | 12/2005 | Hassler | | 2008/0027269 A1 | 1/2008 | Gertner |
| 2005/0288740 A1 | 12/2005 | Hassler, Jr. et al. | | 2008/0027469 A1 | 1/2008 | Bachmann |
| 2006/0015138 A1 | 1/2006 | Gertner | | 2008/0071306 A1 | 3/2008 | Gertner |
| 2006/0020298 A1 | 1/2006 | Camilleri et al. | | 2008/0097496 A1 | 4/2008 | Chang et al. |
| 2006/0041183 A1 | 2/2006 | Massen et al. | | 2008/0108862 A1 | 5/2008 | Jordan et al. |
| 2006/0074439 A1 | 4/2006 | Garner et al. | | 2008/0147002 A1 | 6/2008 | Gertner |
| 2006/0074473 A1 | 4/2006 | Gertner | | 2008/0161717 A1 | 7/2008 | Gertner |
| 2006/0089571 A1 | 4/2006 | Gertner | | 2008/0161875 A1 | 7/2008 | Stone |
| 2006/0122147 A1 | 6/2006 | Wohlrab | | 2008/0166028 A1 | 7/2008 | Turek et al. |
| 2006/0142700 A1 | 6/2006 | Sobelman et al. | | 2008/0167647 A1 | 7/2008 | Gertner |
| 2006/0142790 A1 | 6/2006 | Gertner | | 2008/0167648 A1 | 7/2008 | Gertner |
| 2006/0161139 A1 | 7/2006 | Levine et al. | | 2008/0172072 A1 | 7/2008 | Pool et al. |
| 2006/0161186 A1* | 7/2006 | Hassler et al. ................. 606/153 | | 2008/0188766 A1 | 8/2008 | Gertner |
| 2006/0167531 A1 | 7/2006 | Gertner et al. | | 2008/0195092 A1 | 8/2008 | Kim et al. |
| 2006/0173238 A1 | 8/2006 | Starkebaum | | 2008/0208240 A1 | 8/2008 | Paz |
| 2006/0173424 A1 | 8/2006 | Conlon | | 2008/0221598 A1 | 9/2008 | Dlugos et al. |
| 2006/0178555 A1 | 8/2006 | Bortolotti | | 2008/0243071 A1 | 10/2008 | Quijano et al. |
| 2006/0183967 A1 | 8/2006 | Lechner | | 2008/0249806 A1 | 10/2008 | Dlugos |
| 2006/0189887 A1 | 8/2006 | Hassler, Jr. et al. | | 2008/0250340 A1 | 10/2008 | Dlugos et al. |
| 2006/0189888 A1 | 8/2006 | Hassler, Jr. et al. | | 2008/0250341 A1 | 10/2008 | Dlugos et al. |
| 2006/0189889 A1 | 8/2006 | Gertner | | 2008/0255403 A1 | 10/2008 | Voegele et al. |
| 2006/0194758 A1 | 8/2006 | Lebreton | | 2008/0255414 A1 | 10/2008 | Voegele et al. |
| 2006/0195139 A1 | 8/2006 | Gertner | | 2008/0255425 A1 | 10/2008 | Voegele et al. |
| 2006/0197412 A1 | 9/2006 | Rasmussen | | 2008/0255459 A1 | 10/2008 | Voegele et al. |
| 2006/0199997 A1 | 9/2006 | Hassler, Jr. et al. | | 2008/0255537 A1 | 10/2008 | Voegele et al. |

| Publication No. | Date | Inventor |
|---|---|---|
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2087862 | 8/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09048 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/70131 | 9/2001 |
| WO | WO 01/85071 | 11/2001 |
| WO | WO 02/05753 | 1/2002 |

| | | |
|---|---|---|
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/109300 | 9/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and in clipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Surgery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224;2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery;.V. 11, pp. 327-329, 2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; "Gastrointestinal Factors in Hunger and Satiety." Neuroscience and Behavioral Reviews; V. 6; pp. 145-164; 1982.

Iverson et al.; "Recent Advances in Microscale Pumping Technologies: A Review and Evaluation"; Microfluid Nanofluid; vol. 5; pp. 145-174; Feb. 19, 2008.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qian et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98; 1994.

Small et al.; "Gut hormones and the control of appetite"; Trends in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptide1 secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

Brown et al; "Symmetrical Pouch Dilation After Laparoscopic Adjustable Gastric Banding: Incidence and Management"; Obesity Surgery; V. 18, pp. 1104-1108; 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Neary et al.; "Peptide YY(3-36) and Glucagon-Like Peptide-$1_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

U.S. Appl. No. 12/705,245, filed Feb. 12, 2010, Birk, et al.

* cited by examiner

REMOTELY ADJUSTABLE GASTRIC BANDING SYSTEM

FIELD

The present invention generally relates to medical systems and apparatus and uses thereof for treating obesity and/or obesity-related diseases, and more specifically, relates to gastric banding systems that are remotely adjustable.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, the food is held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction. Naturally, it would be desirable to allow for non-invasive adjustment of gastric band constriction, for example, without the use of a hypodermic needle.

Birk, et al., U.S. Patent Pub. No. 2010-0010291, and Birk, et al., U.S. Ser. No. 12/705,245, which are commonly-assigned and co-pending with the present application, are incorporated herein in their entirety by this specific reference. Both of these applications disclose certain approaches to implantable pumping systems that may be relevant.

Jordan, et al., U.S. Patent Application Pub. Nos. 2008/0108862 and 2005/0104457, and Jordan, et al., U.S. Pat. No. 7,314,443 generally disclose an implantable device that utilizes a stepper motor to move a fluid utilized by the implantable device. However, these documents do not disclose a system for changing a diameter of a reservoir to inflate an inflatable portion of a gastric band.

Bachmann, U.S. Patent Application Pub. Nos. 2008/0002746 and 2005/0251182, Bachmann, et al., U.S. Patent Application Pub. Nos. 2005/0143766 and 2005/0143765, and Bachmann, U.S. Pat. No. 7,238,191 generally disclose a surgical ring that has an adjustable diameter. The diameter is adjusted using a screw thread that lengthens and shortens using a motor. However, these documents do not disclose a system for moving fluid from a reservoir to an inflatable portion of a gastric band.

Forsell, U.S. Patent Application Pub. No. 2001/0011543 and Forsell, U.S. Pat. No. 6,210,347, generally disclose an adjustable implantable device for restricting an opening in the body that food passes through. The implantable device is mechanically adjustable, but these documents do not disclose a system for adjusting the implantable device using fluid from a flexible reservoir.

Some mechanically adjustable implantable devices have a disadvantage of becoming inoperable if the adjustment mechanism fails. Furthermore, because the motor and the driving mechanisms are located near the restricting band itself, they are more subject to strain and damage from the implantation process. Therefore, it is desirable to develop a remotely adjustable gastric band where the motor is separated from the restricting band to reduce the strain from the implantation process such that the risk of damage during implantation is decreased.

Some attempts have been made to use piezoelectric pumps to drive fluid into an inflatable portion of a gastric band, but these pumps may not provide sufficient pumping power and/or may not satisfy other design specifications. Thus, it is desirable to develop a more efficient pumping mechanism.

Additionally, some attempts have been made to utilize a piezoelectrically driven bellows infuser to inflate an inflatable portion of a gastric band. However, these bellows infusers do not offer a reduced area against which pressure is applied after an amount of fluid has been pumped into the gastric band, which may result in higher power requirements and more energy dissipation. Therefore, it is desirable to develop a pumping mechanism that offers efficiencies as fluid is moved from a reservoir to a gastric band.

Further, some attempts have been made to measure pressure in various components of implantable systems. But these pressure measurements have generally been limited to measuring pressure in an injection port or in an organ such as the stomach. Therefore, it is desirable to develop a flexible reservoir with a means for measuring the pressure in the reservoir itself.

Thus, there continues to remain a need for more effective implantable pump systems for use with adjustable gastric bands, particularly such implantable pump systems with increased and more efficient pumping capability.

SUMMARY

Generally described herein are remotely adjustable and powered gastric banding systems. The apparatus and systems described herein aid in facilitating obesity control and/or treating obesity-related diseases while being non-invasive once implanted.

In one embodiment, an implantable system comprises a housing that has a fluid inlet/outlet and a flexible reservoir positioned within the housing. The flexible reservoir is coupled to an inflatable portion of a gastric band via the fluid inlet/outlet. The flexible reservoir contains a fluid and has an expanded configuration and a contracted configuration.

A movable wall is slidably positioned around the flexible reservoir and forms a cylinder around the flexible reservoir. The movable wall has a diameter that may be changed by moving the ends of the movable wall. A driving mechanism, such as a flexible screw, is positioned around the movable wall, and is capable of changing the diameter of the movable wall to compress the flexible reservoir from the expanded configuration to the contracted configuration. When the flexible reservoir is compressed, a portion of the fluid in the flexible reservoir moves into the inflatable portion of the gastric band. The implantable system may also move the fluid out of the inflatable portion of the gastric band. A motor, coupled to the driving mechanism, may actuate the driving mechanism.

In an embodiment, the movable wall has a first end and a second end. The first end of the movable wall and the second end of the movable wall may be freely movable within the housing, or one of the two ends may be fixed to the housing. Furthermore, one end of the flexible screw may be attached to the housing.

Additionally, in an embodiment, the implantable system comprises a compressible structure positioned within the flexible reservoir. The compressible structure facilitates stabilizing boundaries of the flexible reservoir. The compressible structure may be selected from a group consisting of a tube, a sponge material, a synthetic material, a flexible material, and combinations thereof.

A sensing coil unit may be located near the sternum of a patient and may communicate with an external controller via radio frequency signals. The sensing coil unit may provide power and communications to the motor.

In various embodiments, a spring may be positioned around the movable wall to facilitate moving the movable wall. For example, the spring may be an elastic spring, a polymer spring, a stretchable spring, a coplanar spring, a sheath spring, an enclosing spring and/or combinations thereof. The spring may resist or assist the motor in expanding or contracting the movable wall.

DETAILED DESCRIPTION

The present invention generally provides remotely adjustable gastric banding systems, for example, for treatment of obesity and obesity related conditions, as well as systems for controlling inflation of gastric banding systems.

A remotely adjustable gastric band is a medical device which allows a healthcare worker to adjust a gastric band without utilizing hypodermic needles to connect to an implanted access port. An external, handheld controller can be used to send radio frequency signals for powering and communicating with the implanted device. The implanted device can fill or drain the gastric band as requested by the healthcare worker via the handheld controller. The handheld controller may be a remote device configured to produce a telemetric signal that controls the various components of the gastric banding system.

The filling and draining of the band is accomplished by a set of fluidic elements including pumps, valves, and sensors which monitor and/or move fluid between the gastric band and a reservoir. In accordance with various embodiments, different numbers, types, and orientations of the fluidic elements may be utilized to obtain the desired results. Any and/or all of these various components may be configured to be controlled by a remote transmitter, such as a handheld controller.

Figure 1:
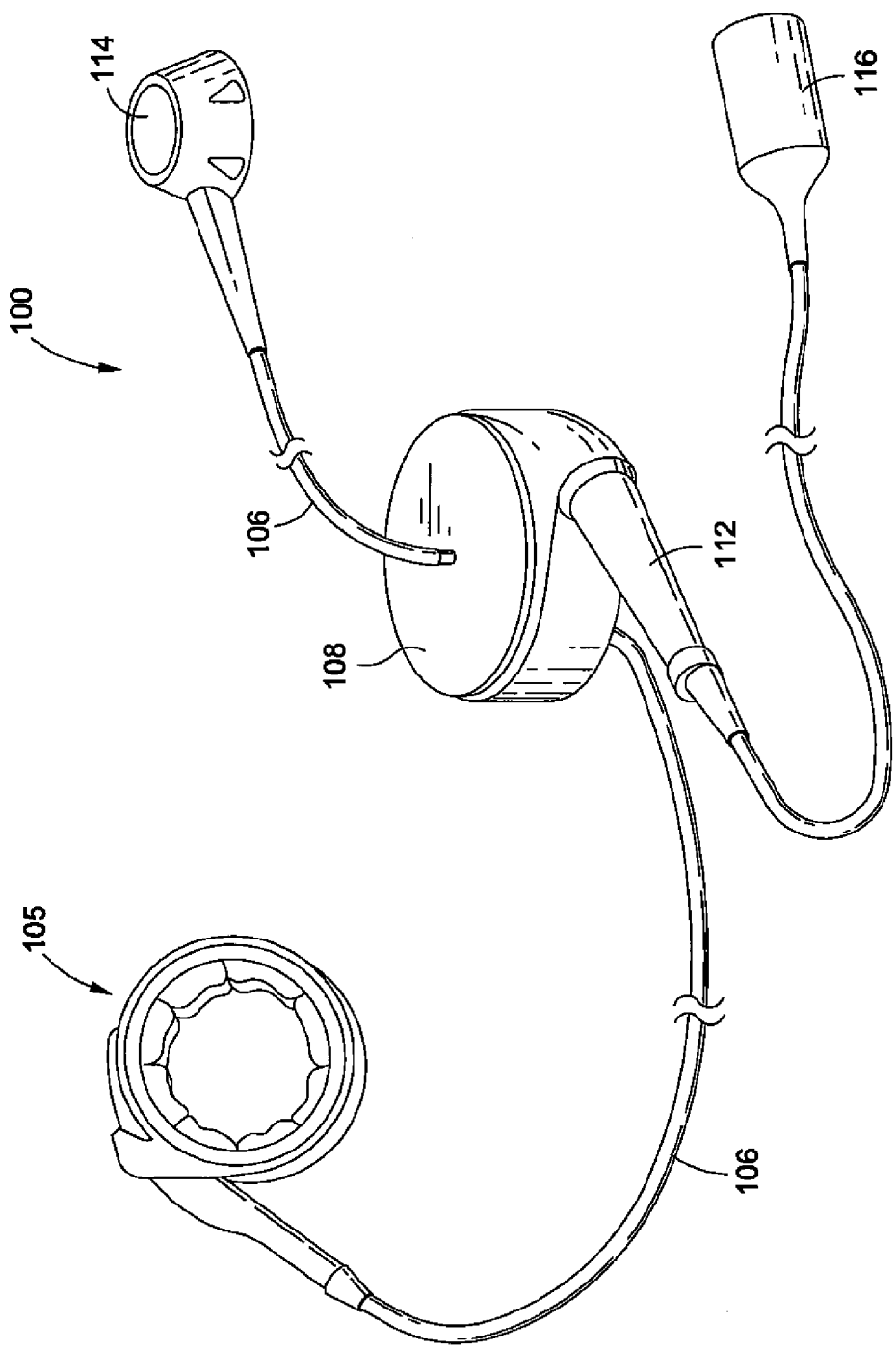
FIG. 1 illustrates a gastric banding system according to an embodiment of the present invention.

Turning now to FIG. 1, a gastric banding system 100 includes a gastric band 105, a reservoir unit 108, a motor housing 112, an access port 114, and a receiving coil unit 116. The flexible tubing 106 connects the gastric band 105 and the access port 114 to the reservoir unit 108. Each of the components of the system 100 is implantable in a patient using conventional surgical techniques. The reservoir unit 108 and the coil unit 116 may be used instead of or in addition to the conventional access port 114.

The reservoir unit 108 may move precisely metered volumes of fluid (e.g., saline, a drug, and/or combinations thereof) from the reservoir unit 108 through the flexible tubing 106 into the gastric band 105. The reservoir unit 108 may comprise a compressible reservoir, such as an elastic polymer, a balloon, a rubber container, a silicone container, a collapsible container, a non-elastomeric container, a bellows, and combinations thereof that are configured to contain the fluid. The motor housing 112 includes a motor configured to compress the compressible reservoir in order to fill or drain the gastric band 105.

Moving the fluid into the gastric band 105 causes inflation of at least one bladder, or inflatable member of the gastric band 105 and constricts around the cardia, or upper portion of the stomach, forming a stoma that restricts the passage of food into a lower portion of the stomach. This stoma can provide a patient with a sensation of satiety or fullness that discourages overeating. In contrast, moving the fluid out of at least one inflatable member of the gastric band 105 contracts the pressure around the cardia and allows a stoma to be at least partially released and regains the patient's hunger sensation.

The receiving coil 116 receives radio frequency signals from an external/remote handheld controller or transmitter to control operation of the system 100. Although "transmitter" may be used herein, it should be understood that the remote transmitter may also be a wireless receiver and/or transceiver operable to take readings from the system 100 to determine the amount of fluid entering and/or exiting the gastric band 105, and/or to send or receive other types of information associated with the gastric banding system 100.

In various embodiments, the remote transmitter provides access to system data and functions and is an external, handheld, reusable battery-powered device. The remote transmitter can be made of any rugged plastic material including, polypropylene, cyclicolephin co-polymer, nylon, and other compatible polymers and the like. Further, the remote transmitter has a user interface including at least one display and at least one user input. The remote transmitter permits a clinician or a patient to navigate through menu driven screens used for data entry, data collection, and control of the gastric banding system 100.

The remote transmitter is capable of communicating with the gastric banding system 100. "Capable of communicating" as used herein refers to the remote transmitter's ability to establish communications with the gastric banding system 100, yet still have the ability to break communication and the systems described herein still function. To establish communication, in one example embodiment, once the remote transmitter is initialized, a display shows a searching query for a nearby gastric banding system 100. As the remote transmitter is brought into range of the gastric banding system 100, the display shows the strength of the communication link. Once stable communications have been acquired, the display shows the serial number (or other unique patient data) of the system so a clinician can verify they have the appropriate patient records in hand. If the patient requires a tightening of the gastric band 105, the clinician can enter the amount of the desired volume increase. The remote transmitter can also display the current volume within the gastric band 105 and indicate the new volume as the gastric band 105 fills. The remote transmitter can also indicate desired and actual volumes during the gastric band 105 draining.

In accordance with various embodiments, the gastric banding system 100 allows for a remotely controlled adjustment without needles, non-invasively, by using the remote transmitter. A conventional access port 114 may be included as part of system 100 in order to provide alternate filling and draining capabilities, for example, to provide a fail-safe alternative in case the non-invasive functionality (e.g., motor, electronics, driving mechanism) becomes inoperative and/or ineffective. The access port 114 may be used to extract fluid from the system in case of an emergency or as a safety measure. However, non-invasively filling and draining the gastric band 105 using the reservoir unit 108 represents advantages over gastric banding systems that only use standard access ports. The access port 114 may further be used to prime the system with a desired amount of fluid upon implantation.

When compared to conventional gastric banding systems having standard access ports which exclusively require syringe access, the presently described systems and apparatus offer several benefits. First, for conventional access ports located under a thick layer of fatty tissue, which is generally the case as the devices are typically used to treat obesity, the access port can be difficult to locate. The present systems reduce or eliminate the need for port location as the use of the remote transmitter removes the necessity of adjustment using a syringe.

Secondly, accessing the access port in conventional systems, when there is ambiguity on its location, can cause damage by accidentally puncturing the tubing which connects the access port to the gastric band. This damage can require another surgery in order to repair the punctured tubing. Further, when a conventional access port cannot be located by palpation, x-ray imaging may be required to guide a needle into the access port. Such imaging practices put a patient at risk for x-ray radiation exposure. The present systems and apparatus remove the need for these unnecessary procedures and save the patient from x-ray radiation exposure. As described herein, the present systems and apparatus may be compatible with magnetic resonance imaging (MRI), which is much safer for a patient.

The fluids used within the systems include any fluid that is biocompatible and incompressible. The fluid has no adverse effect on the patient in the unlikely event that a leak emanates from the system. The fluid can simply be water or any biocompatible polymer oil such as castor oil. In an example embodiment, the fluid is saline, a drug, and/or combinations thereof. The tubing 106 connects certain components of the system 100 and comprises any biocompatible flexible tubing that does not degrade in vivo. The tubing 106 is configured to withstand hydraulic forces up to hundreds of psi without leakage.

Figure 2A:
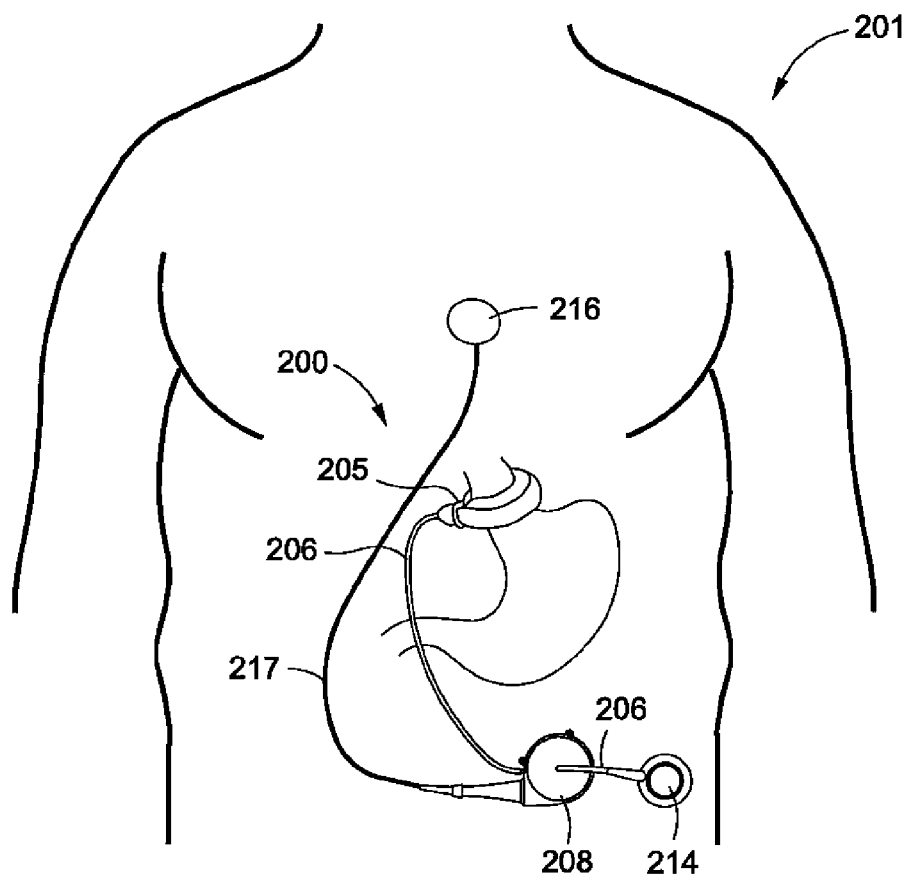
FIGS. 2A and 2B illustrate a location of a gastric banding system within a patient's body according to an embodiment of the present invention.
Figure 2B:
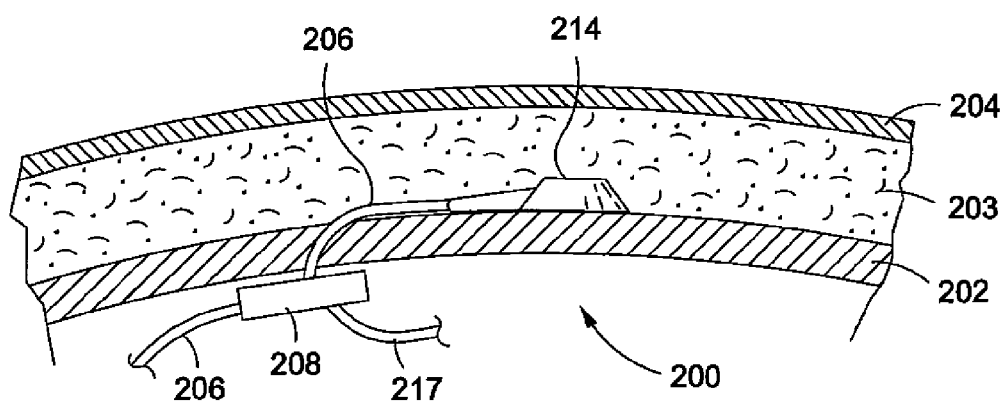

According to various embodiments, and with reference to FIGS. 2A-2B, components of the gastric banding system 200 may be placed in their respective positions within a patient 201 using common surgical techniques. The surgical techniques may be similar to those used in the placement of conventional gastric banding systems. For example, the gastric band 205 may be placed around the stomach using laparoscopic techniques, as known to those of skill in the art.

Like a conventional access port, various components of the gastric banding system 200 may be sutured onto the rectus muscle sheath 202 or any other conveniently accessible muscle. For example, the access port 214 and/or the reservoir unit 208 may be sutured to the rectus muscle sheath 202. The rectus muscle sheath 202 provides a secure surface on which to attach the access port 214 under a layer of fat 203 that separates the patient's skin 204 from the muscle 202.

The receiving coil unit 216 may be located near the sternum of the patient 201, and a wire 217 may electronically couple the receiving coil unit 216 to the reservoir unit 208. In an embodiment as illustrated in FIGS. 2A-2B, the reservoir unit 208 is located in the peritoneal cavity of the patient 201. In other embodiments, the components of system 200 may be positioned in other locations in the patient 201 to facilitate filling or draining of the gastric band 205. For example, in an embodiment, the access port 214 may be incorporated into the housing 208, such that the housing 208 may be implanted on the rectus muscle sheath.

Figure 3A:
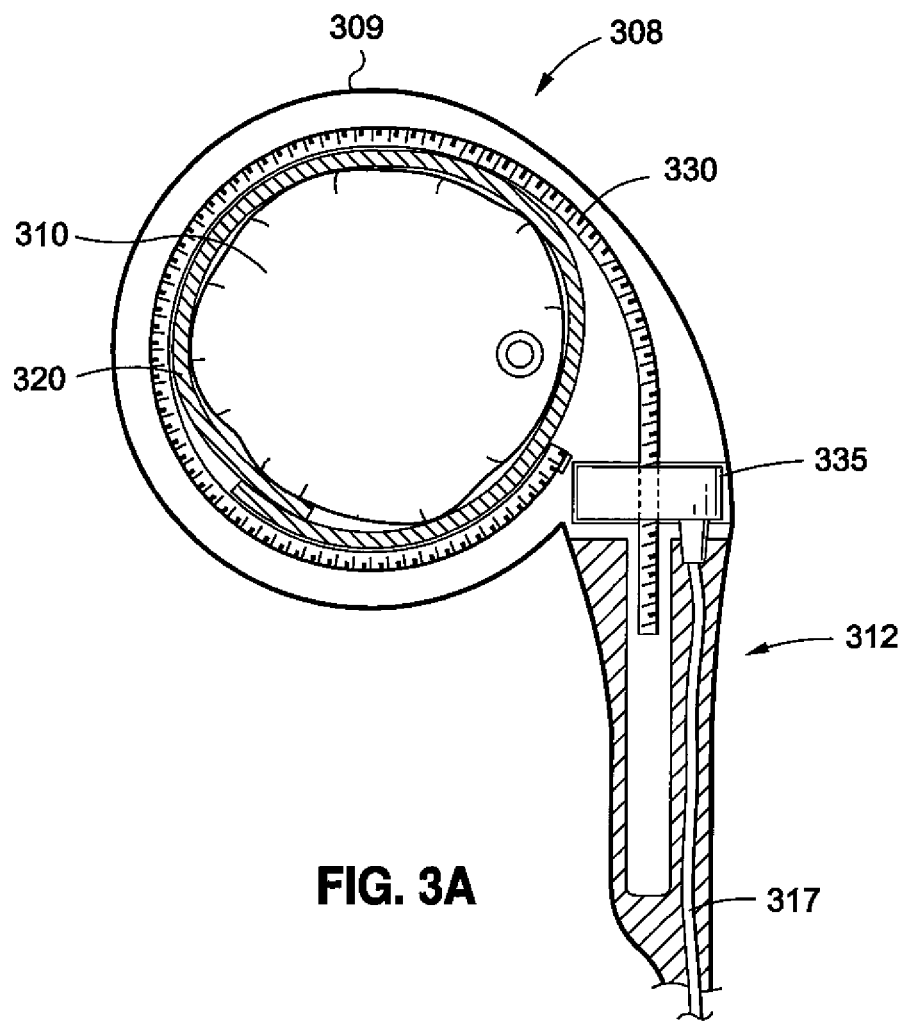
FIG. 3A illustrates a top, cross-sectional view of a reservoir unit according to an embodiment of the present invention.
Figure 3B:
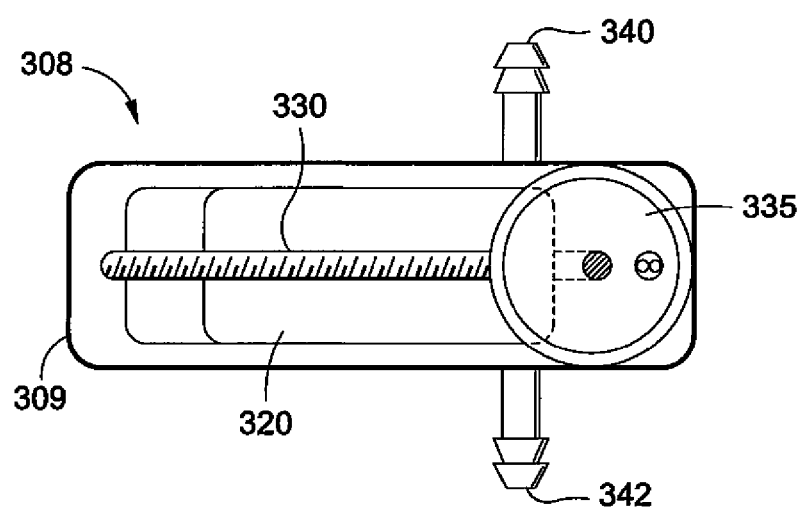
FIG. 3B illustrates a side, cross-sectional view of the reservoir unit of FIG. 3A according to an embodiment of the present invention.

Turning to FIGS. 3A-3B, in an embodiment, the reservoir unit 308 comprises a housing 309 that is rigid and generally cylindrical in shape. A flexible pouch or reservoir 310 is disposed in the housing 309. The flexible pouch 310 may be a compressible pouch, an elastic polymer, a balloon, a rubber container, a silicon container, and/or combinations thereof. Further, the flexible pouch 310 may be formed in the shape of a donut, a circle, an ellipse, a rectangle, and combinations thereof.

A movable wall 320 wraps around the flexible pouch 310, with one end of the movable wall 320 overlapping the other end of the movable wall 320 such that the movable wall 320 forms a cylinder within which the flexible pouch 310 is located. Although "cylinder" is used to describe the shape of the movable wall 320 in the reservoir unit 308, it should be understood that the movable wall 320 may form any shape that is capable of compressing or expanding the flexible pouch 310. For example, the movable wall 320 may form an extended ellipse, oval, rectangle or other shape.

The movable wall 320 may have a constant height and/or thickness, or it may have a variable height and/or thickness. In an embodiment, the movable wall 320 may be disposed and/or covered in a material that reduces friction between the overlapping ends of the movable wall 320. For example, the movable wall 320 may be wrapped in a shrinkable Teflon (PTFE) tube.

As the ends of the movable wall 320 overlap to a greater extent, the diameter of the cylinder formed by the movable wall 320 decreases. Although "diameter" is used to describe a dimension of a cylinder, it should be understood that other geometric shapes of the movable wall 320 have other characteristic dimensions, and these dimensions may change as the movable wall 320 compresses or expands the flexible pouch 310.

The size and/or volume of the flexible pouch 310 decreases as the ends of the moveable wall 320 overlap to a greater degree. As the size of the flexible pouch 310 decreases, fluid is expelled from the flexible pouch 310 and is moved into the gastric band. On the other hand, as the diameter of the cylinder created by the movable wall 320 increases (i.e., the ends of the movable wall 320 overlap less), the size and/or volume of the flexible pouch 310 increases and fluid is drawn out of the gastric band into the flexible pouch 310.

The reservoir unit 308 comprises an inlet/outlet port 340 for allowing fluid to pass bidirectionally between the flexible pouch 310 and the access port. The reservoir unit further comprises an inlet/outlet port 342 for allowing fluid to pass bidirectionally between the flexible pouch 310 and the gastric band. The ports 340 and 342 are barbed to facilitate attachment to the flexible tubing and to allow bidirectional flow of the fluid into and out of the flexible pouch 310. The ports 340 and 342 may comprise one or more flow control devices for controlling movement of the fluid into or out of the flexible pouch 310. The flow control devices may be a valve, a tube, a regulator, and/or combinations thereof. Other embodiments may not include a flow control device.

In an embodiment, a motor 335 is disposed within the motor housing 312, and the motor 335 drives a driving mechanism 330, such as a rod, a string, a screw, or combinations thereof. In an embodiment, the driving mechanism 330 comprises a flexible screw, and in other embodiments, the driving mechanism 330 is partially a flexible screw and partially a string, a cord, a rod, a cable, or other flexible member. The motor 335 is coupled to the receiving coil unit via a wire 317. The motor 335 may be a piezoelectric motor, an electromagnetic motor, an AC motor, a DC motor, a stepper motor, and/or combinations thereof. Furthermore, the motor 335 may move the driving mechanism 330 by rotational and/or translational movement.

The driving mechanism 330 wraps around the movable wall 320 to facilitate increasing or decreasing the diameter of the cylinder formed by the movable wall 320. For example, as the driving mechanism 330 exits the housing 309 of the reservoir unit 308 through the motor 335 and into the motor housing 312, the diameter of the cylinder formed by the movable wall 320 decreases. Similarly, as the driving mechanism 330 enters the housing 309 of the reservoir unit 308, the diameter of the cylinder formed by the movable wall 320 increases.

The driving mechanism 330 may enter the housing 309 through the motor 335, and the motor may extend and withdraw the driving mechanism 330 into and out of the housing 309. The driving mechanism 330 wraps around the movable wall 320 to facilitate changing the diameter of the cylinder formed by the movable wall.

In one embodiment, as illustrated in FIG. 3A, one end of the driving mechanism 330 attaches to the housing 309 near the point where the mechanism 330 enters the housing 309, or near the motor 335. The mechanism 330 may pass through a loop or other guiding structure on the movable wall 320 to facilitate expanding and contracting of the diameter of the movable wall 320. In other embodiments, the driving mechanism 330 may not be attached or connected to the movable wall 320.

With one end of the driving mechanism 330 fixed to the housing 309, as the motor 335 draws the driving mechanism 330 out of the housing 309 and into the motor housing 312, the total length of the driving mechanism 330 in the housing 309 decreases, which causes the ends of the movable wall 320 to overlap to a greater degree. This greater overlap causes the size and/or volume of the flexible pouch 310 to decrease. In this configuration, where one end of the driving mechanism 330 is fixed to the housing 309, the motor 335 may be capable of exerting a greater force on the driving mechanism 330 than in the configuration where the driving mechanism 330 is attached directly to the movable wall 320. Thus, more friction between the overlapping ends of the movable wall 320 may be overcome where the driving mechanism 330 is fixed to the housing 309.

The movable wall 320 may move freely within the housing 309. In an embodiment, the movable wall 320 may move within tracks, guides, and/or paths in the housing 309. In another embodiment, guide posts or bearings may be utilized to guide the motion of the movable wall 320 within the housing 309.

As noted above, the size of the flexible pouch 310 changes as the diameter of the cylinder formed by the movable wall 320 changes. This change in diameter is accomplished by changing the length of the driving mechanism 330 within the housing 309. Thus, by knowing the length of the driving mechanism 330, either inside or outside the housing 309, the size and/or volume of the flexible pouch 310 may be determined, and accordingly, the amount of fluid within the gastric band may be determined.

In an embodiment, the external controller may display an estimated volume of fluid within the gastric band based on a distance traveled by the driving mechanism 330. The length of the driving mechanism 330 may be advantageously determined to provide a desired range of volumes within the gastric band and/or the flexible pouch 310. Furthermore, a sufficient amount of space within the motor housing 312 and the housing 309 of the reservoir unit 308 is designed to allow the driving mechanism 330 to have the desired range of motion.

In another embodiment, and with reference to FIGS. 4A-4D, the movable wall 420 has a first end 422 that is attached to the housing 409 of the reservoir unit 408. The first end 422 remains stationary with respect to the housing 409 as the driving mechanism 430 is moved into and out of the housing 409. A tab 427 may be utilized to maintain a portion of the movable wall 420 in a fixed position with respect to the housing 409.

A second end 423 of the movable wall 420 is attached to the driving mechanism 430. As the driving mechanism 430 moves into and out of the housing 409, the second end 423 of the movable wall 420 moves with the driving mechanism 430 to cause the first end 422 to overlap to a greater or lesser degree with the second end 423. As the degree of overlap of the first and second ends 422 and 423 increases or decreases, the diameter of the cylinder formed by the movable wall 420 correspondingly decreases and increases, as discussed above.

Although the movable wall 420 may move freely within the housing 409, guides, rods, bearings, and combinations thereof may be utilized to guide the movement of the movable wall 420. For example, with reference to FIG. 4D, in one embodiment, posts 425 are utilized to guide the movable wall 420. The first end 422 of the movable wall 420 may attach to one of the posts 425 (e.g., the second post from the first end 422 of the movable wall 420), and the second end 423 may attach to the driving mechanism 430.

In various embodiments as illustrated in FIGS. 4A-4D, variations of the location of the driving mechanism 430 on the movable wall 420 may be permissible. Because the driving mechanism 430 is attached to the second end 423 of the movable wall, the driving mechanism 430 may still facilitate appropriate movement of the movable wall 420 even if the driving mechanism 430 is not vertically in the center of the movable wall 420.

Figure 4A:
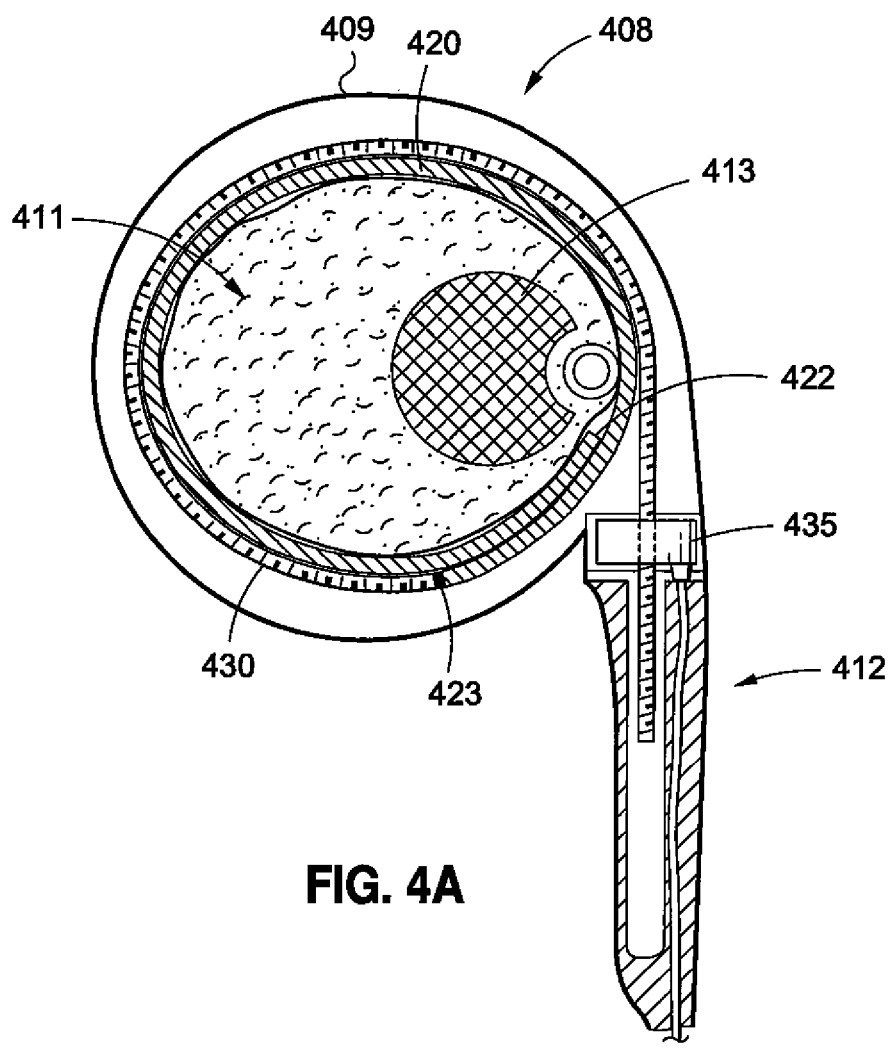
FIG. 4A illustrates a top, cross-sectional view of a reservoir unit with a compressible structure according to an embodiment of the present invention.
Figure 4B:
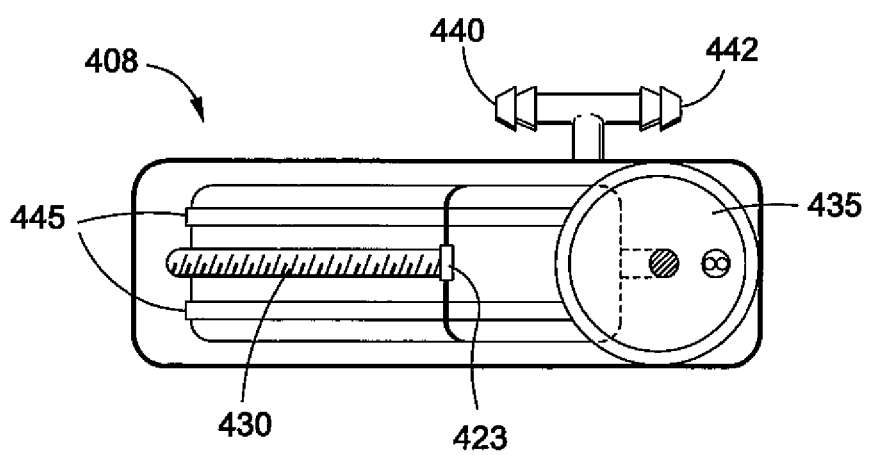
FIG. 4B illustrates a side, cross-sectional view of the reservoir unit of FIG. 4A according to an embodiment of the present invention.
Figure 4C:
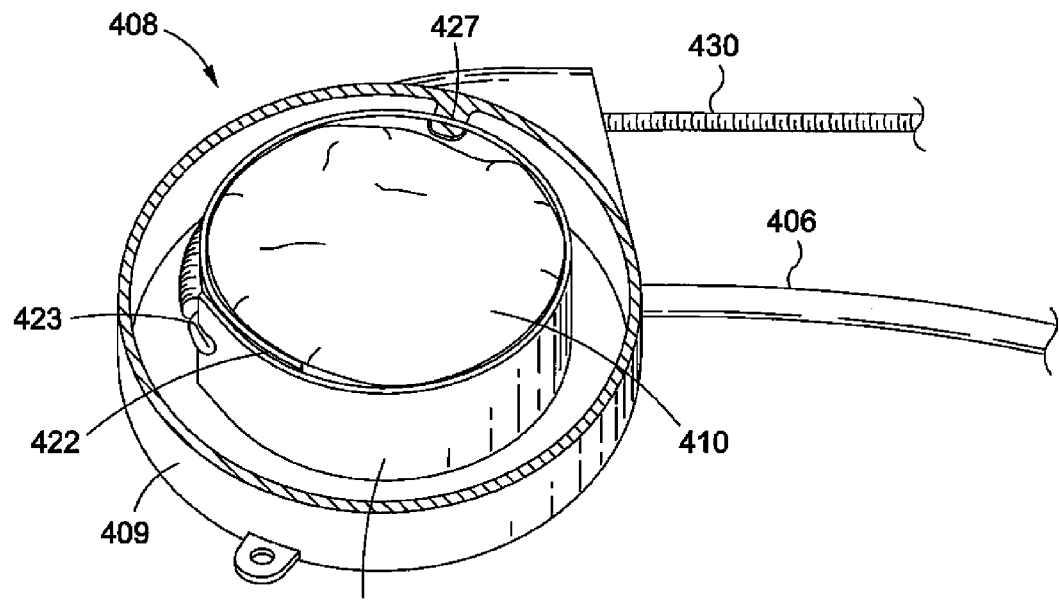
FIG. 4C illustrates a perspective, cut-away view of a reservoir unit having a movable wall according to an embodiment of the present invention.
Figure 4D:
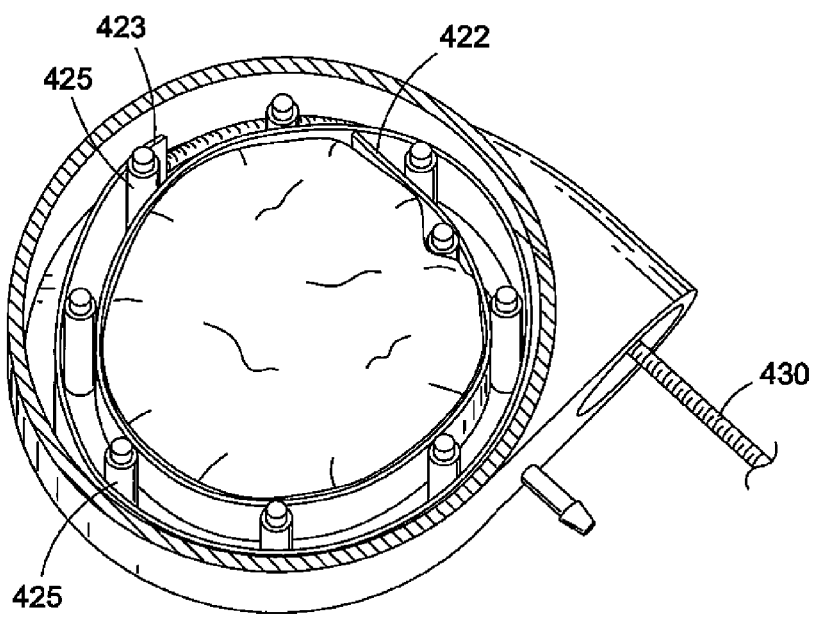
FIG. 4D illustrates a perspective, cut-away view of a reservoir unit having posts to guide a movable wall according to an embodiment of the present invention.

With reference to FIG. 4B, the access port inlet/outlet 440 of the reservoir unit 408 is located on the same side of the reservoir unit 408 as the gastric band inlet/outlet 442. In such a configuration, if the motor 435 and/or the reservoir unit 408 were to fail, the access port can still be used to fill and drain the gastric band. Furthermore, locating the inlets/outlets 440, 442 on the same side of the reservoir unit 408 may prevent occlusions between the access port and the gastric band. In an embodiment, a valve may be located inside the housing 409 to facilitate operation of the inlets/outlets 440, 442. For example, a three way valve may control the fluid flow between the gastric band, inlet/outlets 440, 442, and an access/injection port.

With reference to FIG. 4A, in one embodiment, a flexible and/or compressible structure 411 may be utilized to give shape to and/or stabilize boundaries of the flexible pouch 410 as it expands and contracts to drain and fill the gastric band. Examples of materials that may be utilized to form the structure 411 are tubes, vertical tubes, synthetic materials, sponge materials, flexible materials, and combinations thereof. The structure 411 may comprise any material that allows fluid to enter and exit the flexible pouch 410 and that does not substantially increase the pressure within the flexible pouch 410.

In various embodiments, the cylinder created by the movable wall 420 has a minimum diameter. For example, at a certain point, the driving mechanism 430 may have exited the housing 409 to the greatest extent possible. Because the minimum diameter may be greater than zero given the structure of the movable wall 420, some space may be left in the flexible pouch 410 when the minimum diameter is achieved. If fluid occupies this space, the reservoir unit 408 may be prone to leakage. However, in an embodiment, an internal structure 413 may be located within the flexible pouch 410 to occupy the space remaining when the minimum diameter is achieved. Thus, less fluid will occupy the remaining space, which reduces the chance of a fluid leak. Furthermore, various gages and other components, such as electronics or pressure sensors, may reside within the internal structure 413 to allow the gastric banding system to be more compact. In some embodiments, the flexible pouch 410 may be donut-shaped and/or crescent shaped to accommodate the internal structure 413.

A pressure sensor may be included in the internal structure 413, such that pressures from the gastric band and/or the flexible pouch 410 may be monitored. The pressure sensor provides a non-invasive method for verifying the functionality of the motor and/or the inflation status of the gastric band. The inclusion of a pressure sensor utilizes additional electronics, such as a driver circuit and two-way communications, with possible modifications to the power electronics of the receiving coil unit and modifications to the external controller for displaying pressure data.

In accordance with further embodiments, the motor 435 may provide different amounts of force as the motor 435 moves the driving mechanism 430 into or out of the housing 409. For example, in an embodiment, the motor 435 may provide less force when moving the driving mechanism 430 into the housing 409 (i.e., increasing the volume in the flexible pouch 410) than when moving the driving mechanism 430 out of the housing 409 (i.e., decreasing the volume in the flexible pouch 410 and moving the fluid to the gastric band). Thus, springs 445, such as coplanar springs, elastic bands, polymer springs, stretchable springs, sheath springs, enclosing springs, or other mechanisms, may be utilized to assist in decreasing the volume within the flexible pouch 410. If springs 445 are utilized, they may assist the motor in compressing the flexible pouch 410 in order to move fluid out of the flexible pouch 410. Further, when expanding the flexible pouch 410, the pressure within the gastric band, together with the power provided by the motor 435, may be sufficient to counteract the compressive force of the springs 445 to allow the flexible pouch 410 to expand.

Figure 4E:
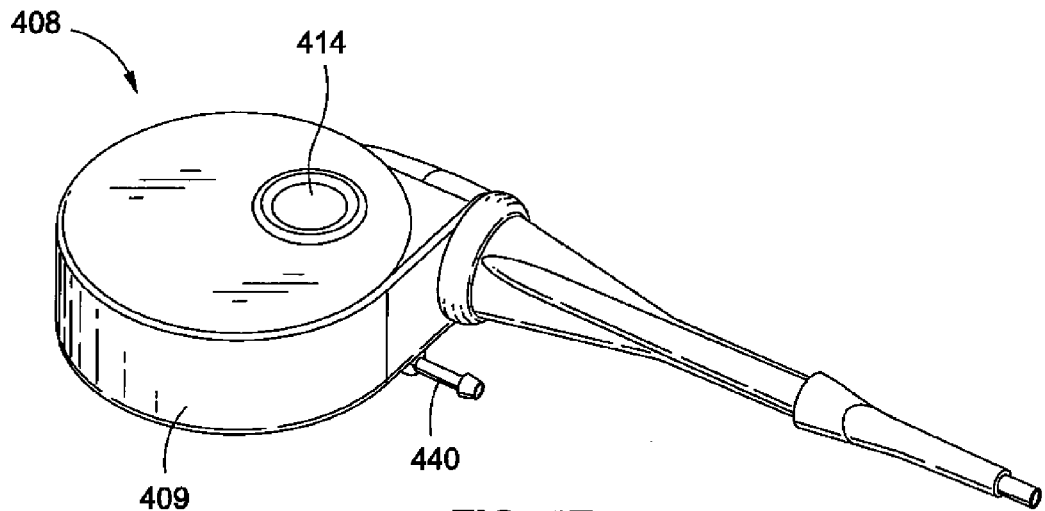
FIG. 4E illustrates a perspective view of a reservoir unit with an access port according to an embodiment of the present invention.
Figure 4F:
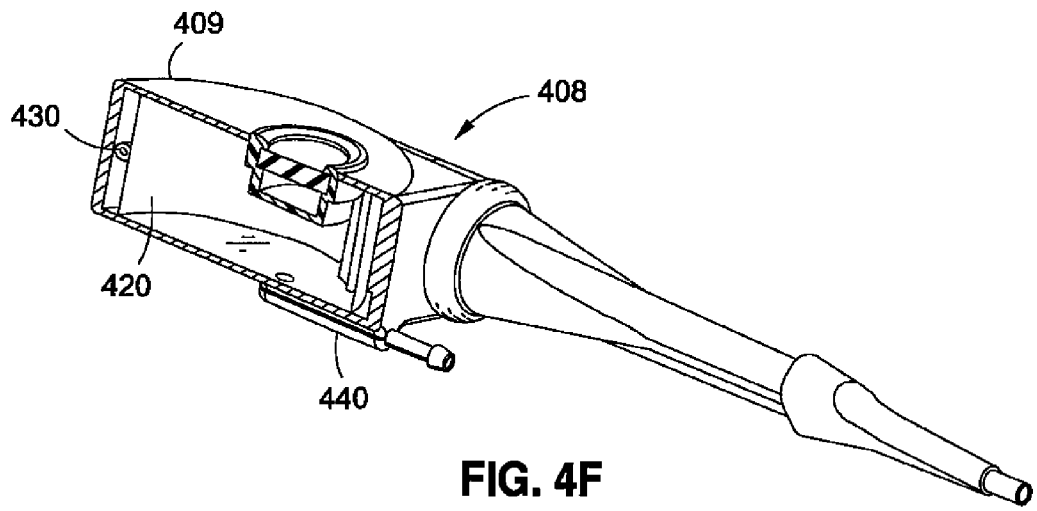
FIG. 4F illustrates a perspective, cut-away view of the reservoir unit with an access port according to FIG. 4E.
Figure 4G:
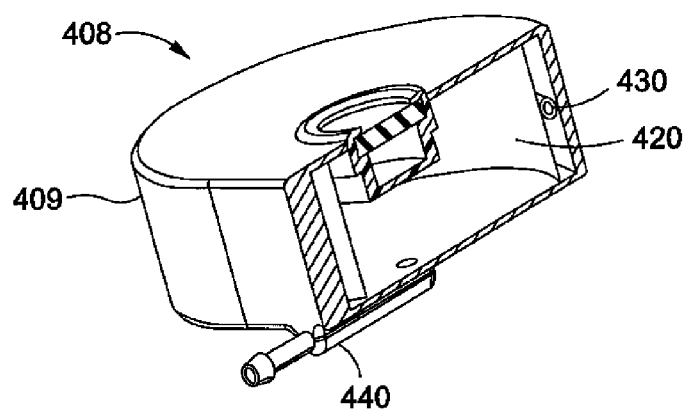
FIG. 4G illustrates another perspective, cut-away view of the reservoir unit with an access port according to FIG. 4E.

Although the embodiments illustrated in FIGS. 3A-3B and FIGS. 4A-4D are illustrated as having fluid inlet/outlets 340, 342, 440, 442 that couple an access port to the flexible pouch 310, 410, it should be understood that the access port may also be incorporated into the housing 309, 409 and may be directly coupled to the flexible pouch 310, 410. For example, as illustrated in FIGS. 4E-4G, an access port 414 is incorporated into the housing 409 of the reservoir unit 408 to facilitate filling and draining the reservoir and/or the inflatable portion of the gastric band. With the access port 414 incorporated into the housing 409, a single fluid inlet/outlet 440 may be utilized to fill and drain the gastric band. Although not shown for simplicity in FIGS. 4F-4G, a flexible pouch may be located within the movable wall 420, and fluidic connections may exist between the flexible pouch, the access port 414, and the fluid inlet/outlet 440.

Figure 5:
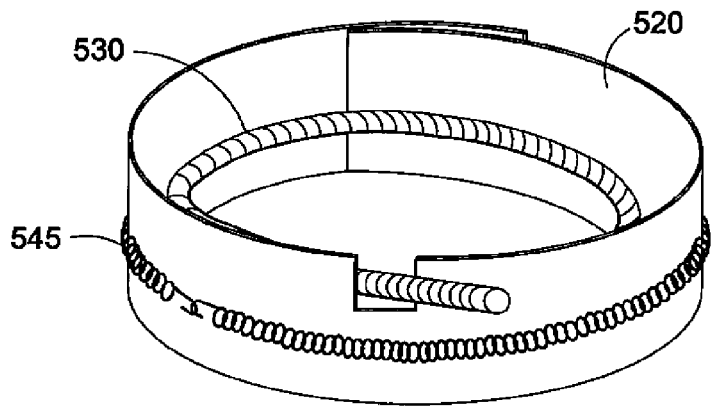
FIG. 5 illustrates a perspective view of a movable wall, a spring, and a driving mechanism according to an embodiment of the present invention.

With reference to FIG. 5, in an embodiment, a compression spring 545 may be utilized to help contract the flexible pouch and expel fluid from the flexible pouch. FIG. 5 illustrates a compression wall 520, the driving mechanism 530, and the compression spring 545, but it should be understood that this assembly may be utilized in connection with the other embodiments disclosed herein. For example, the compression wall 520 may facilitate moving a movable wall that wraps around the flexible pouch. As illustrated in FIG. 5, the driving mechanism 530 passes along the inside of the compression wall 520, and the compression spring 545 wraps around the outside of the compression wall 520 to facilitate modifying the position and/or size of the compression wall 520 and moving fluid into or out of the flexible pouch. In other embodiments, the compression spring 545 and the driving mechanism 530 may be located on the same side of the compression wall 520.

In another embodiment, with reference to FIGS. 6A-6D, a sheath 646 may be utilized to assist in expanding or contracting the flexible reservoir in order to fill or drain the inflatable portion of the gastric band. The sheath 646 may comprise an elastic material such as polymers, soft silicone, or springs. The sheath 646 may be used in conjunction with or in place of the movable wall discussed above. The sheath 646 functions to assist the motor 635 as it compresses or squeezes the flexible reservoir. The sheath 646 also resists the motor 635 as it expands and releases pressure on the reservoir, for example, when draining the inflatable portion of the gastric band. In other embodiments, the sheath 635 may resist contraction and assist expansion of the flexible reservoir.

Figure 6A:
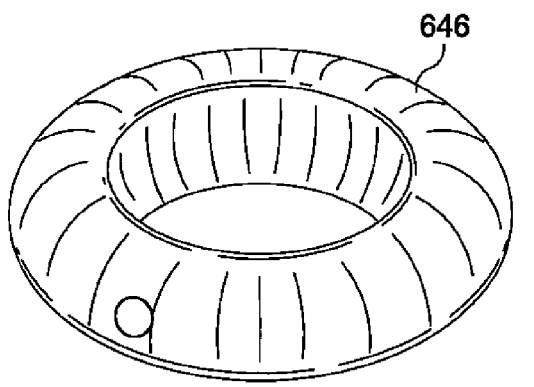
FIGS. 6A-6C illustrate perspective views of a sheath, a driving mechanism, and a motor according to various embodiments of the present invention.
Figure 6B:
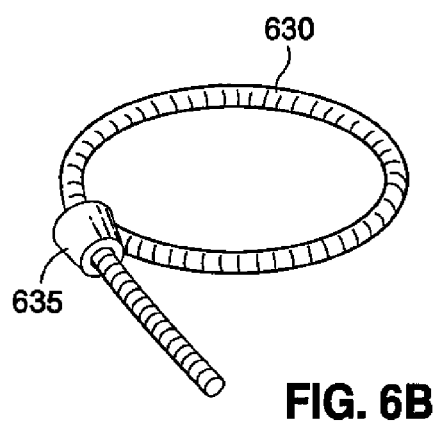
Figure 6C:
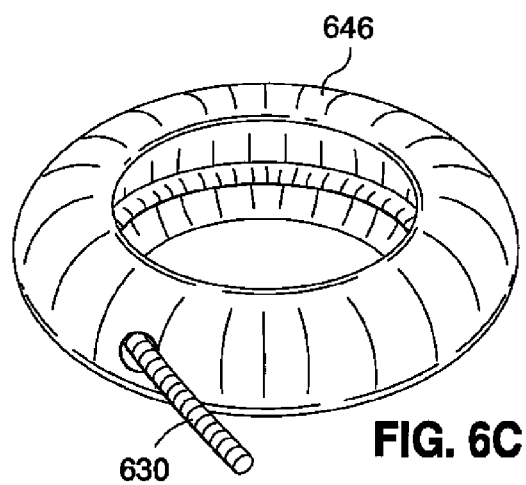
Figure 6D:
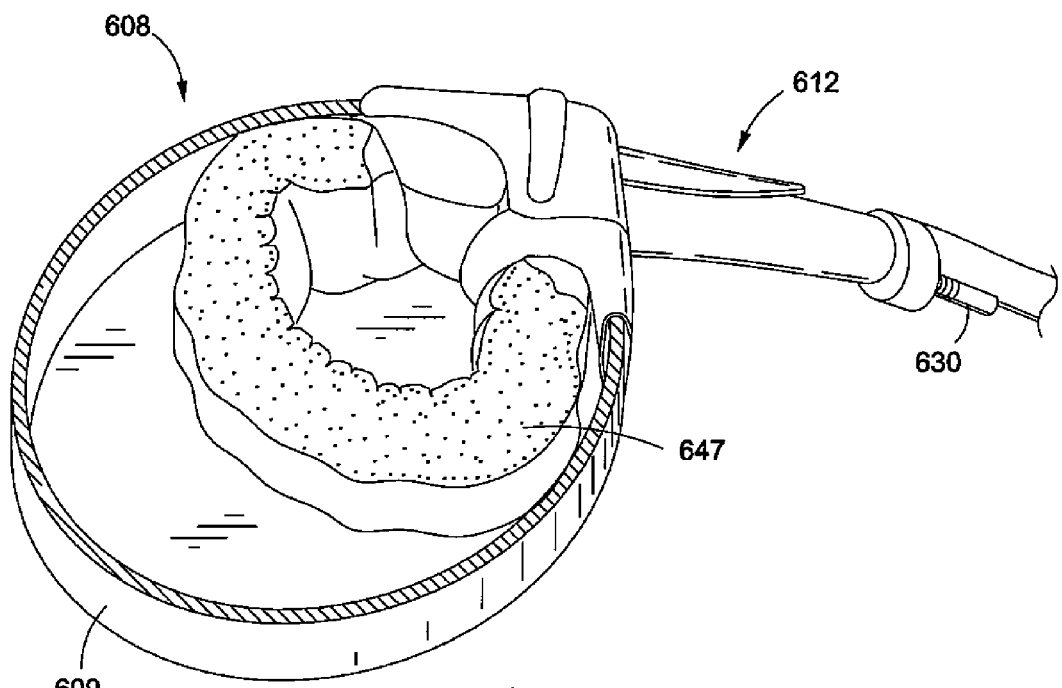
FIG. 6D illustrates a perspective, cut-away view of a reservoir unit having a sheath according to an embodiment of the present invention.

As illustrated in FIG. 6C, the driving mechanism 630 and the motor 635 may be located substantially within the sheath 646. In another embodiment, as illustrated in FIG. 6D, the driving mechanism 630 may be located substantially within a compression sheath 647, and the motor may be located in the motor housing 612. The compression sheath 647 may be utilized in place of a movable wall in order to compress the flexible reservoir. The compression sheath 647 may be made of ePTFE, a foamy material that is rigid in the axis of its cross-section, but compressible and capable of returning to its original length in its longitudinal axis.

The movable wall may comprise different structures and materials according to various embodiments of the present invention. For example, Teflon material may be used for the movable wall, and/or Teflon tape may be utilized to cover the movable wall to reduce friction. In other embodiments, the movable wall may comprise an accordion-type structure. As illustrated in FIG. 6D, the sheath 646 may comprise ePTFE and may be used in place of and/or in addition to the movable wall. Still, in other embodiments, the movable wall may comprise rigid vertical portions circumferentially spaced and connected by thinner flexible portions so that when the movable wall contracts, the flexible portions bend, bringing the vertical portions closer together.

Figure 7:
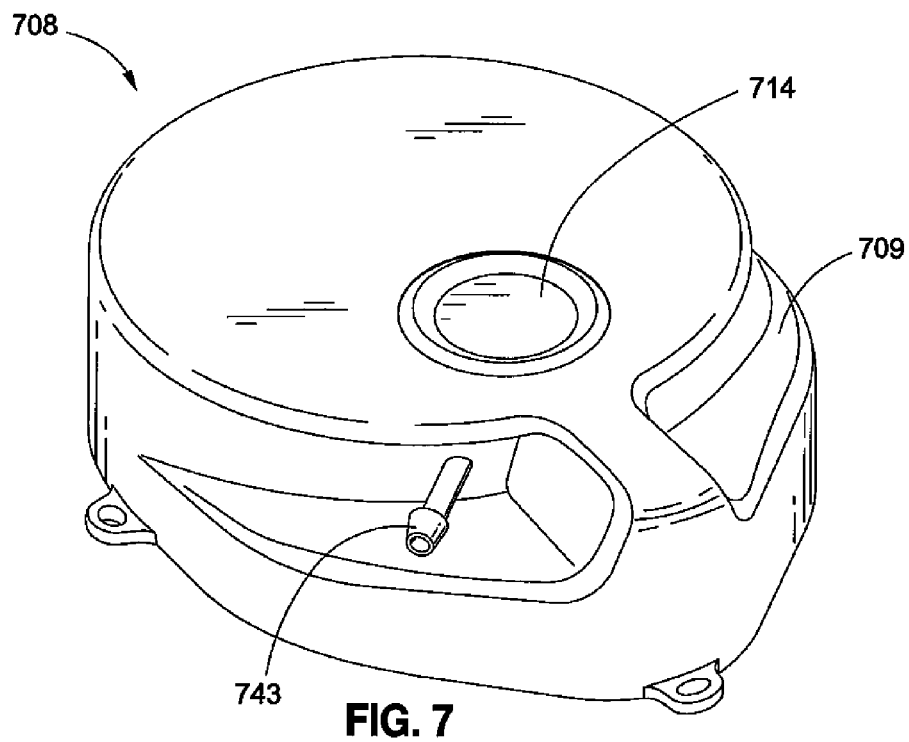
FIG. 7 illustrates a perspective view of a reservoir unit with an access port and/or other components according to an embodiment of the present invention.

In an embodiment, and with reference to FIG. 7, the reservoir unit 708 and the housing 709 may be configured to house various components of the gastric banding system. For example, the access port 714 may be integrated into the reservoir unit 708, and the housing 709 may have one fluid inlet/outlet 743. The fluid inlet/outlet 743 may be used to fill and drain the inflatable portion of the gastric band using either a subcutaneous injection through a needle-penetrable septum of the access port 714, or by using the internal flexible reservoir. Further, the access port 714 may be utilized to fill or drain the flexible reservoir itself using a subcutaneous injection. The reservoir unit 708 may be sutured to the rectus muscle sheath as discussed above. In an embodiment, a sensing coil (for example, similar to the receiving coil 116 in FIG. 1) for power and communications and the corresponding electronics may also be integrated in the housing 709. Further, in an embodiment, the housing 709 may contain all the wires utilized for the reservoir unit 708 such that the wires do not extend from the reservoir unit 708. Containing the wires in this manner aids in MRI compatibility.

As illustrated in FIG. 7, in an embodiment, the driving mechanism (e.g., a flexible screw) may wrap itself around the periphery of the housing 709 as the motor drives the driving mechanism to expand and contract the movable wall and the reservoir. The lower, larger portion of the housing may be considered the motor housing, with the motor being located in the raised portion that connects the lower, larger portion with the upper, smaller portion. The driving mechanism may be configured to wrap around the periphery of the housing 709 without causing interference with the movement of the movable wall.

Figure 8:
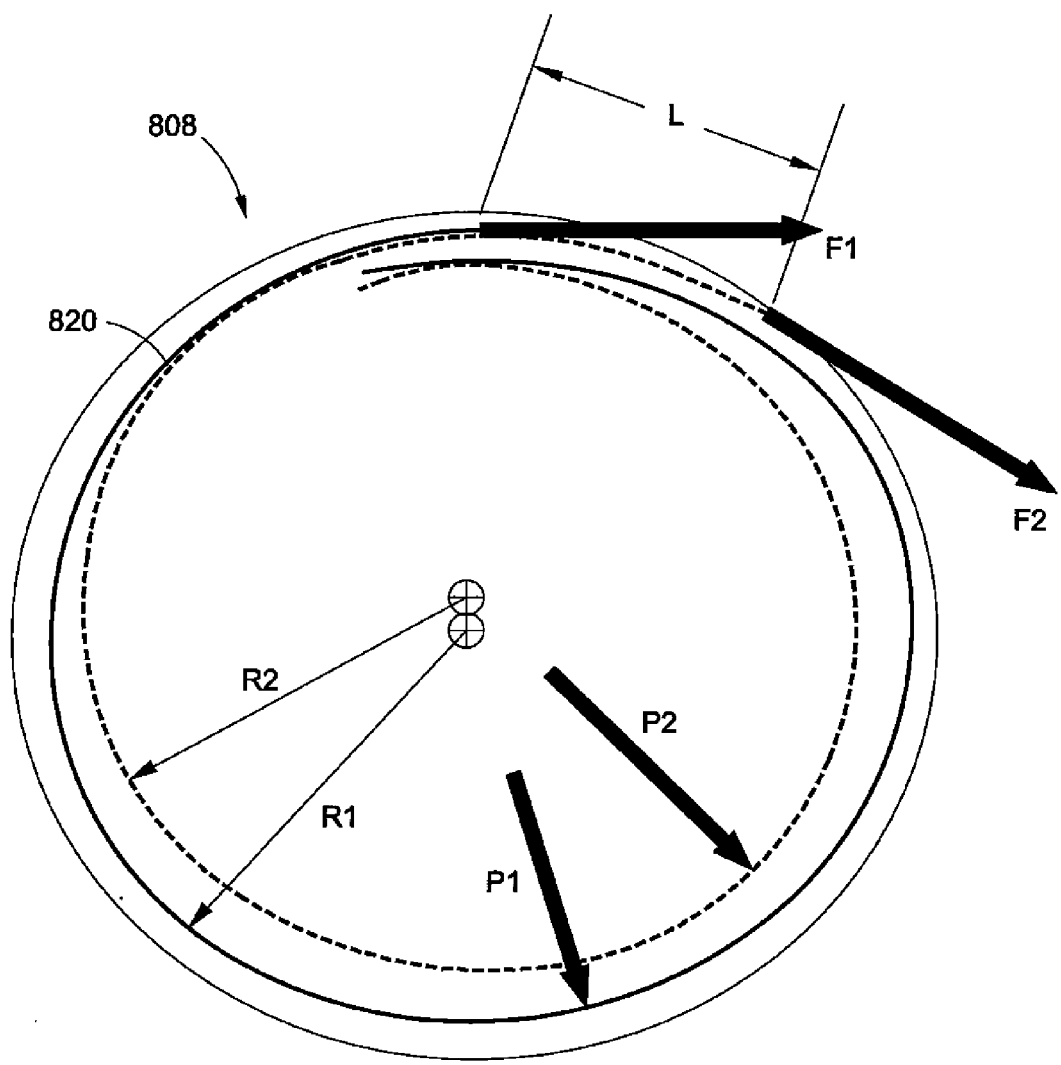
FIG. 8 illustrates a force and pressure diagram of a reservoir unit according to an embodiment of the present invention.

FIG. 8 illustrates some of the forces involved in the reservoir unit 808 according to an embodiment of the present invention. One of skill in the art will appreciate that other forces also are involved in the operation of the reservoir unit 808.

"R1" and "R2" in FIG. 8 illustrate two different radii of the cylinder formed by the movable wall 820. The R1 illustrates a radius of the movable wall 820 in an expanded configuration, and the R2 illustrates a smaller radius of the movable wall 820 in a contracted configuration. The driving mechanism 830 wraps around the movable wall 820, and the "L" represents a travel distance of the driving mechanism 830 that results from change in the radius of the movable wall 820 from R1 to R2. The length L is calculated by the formula $L=2\pi(R1-R2)$. This length, along with knowledge of the pressures P1 and P2, may be used to determine, predict, and/or estimate the forces "F1" and "F2" required by the motor in order to move the movable wall 820 at R1 and R2. Further, the length L may be used to determine, predict, and/or estimate the pressure and/or volume of fluid in the flexible reservoir and/or the inflatable portion of the gastric band.

The pressures "P1" and "P2" represent the pressure exerted by the flexible reservoir against the movable wall 820 when the movable wall 820 is at R1 and R2. As the volume decreases in the flexible reservoir, the surface area of the movable wall 820 against which the pressure is applied decreases (i.e., a decreased diameter of the movable wall 820 leads to a reduced surface area). The resulting force necessary to counteract P1 and P2 and move the driving mechanism 830 is proportional to pressure times the area against which the pressure is applied.

The decrease in area of the movable wall 820 means that less force is utilized to move the driving mechanism 830 at R2 and P2 than at R1 and P1, if the pressure against the movable wall 820 were due solely to fluid in the reservoir. However, because the pressure within the inflatable portion of the gastric band increases with an increased volume, greater force is required to move additional fluid into the gastric band. Thus, the reduced force utilized at R2 and P2 helps to counteract the expected increase in pressure as volume in the gastric band increases. In contrast, where a syringe or plunger-type reservoir is used, the force required to fill the gastric band increases to a greater degree as the gastric band inflates, without any beneficial decrease in the force required to move the constant-area plunger.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable system for use in a gastric band system comprising:
    a housing having a fluid inlet/outlet;
    a flexible reservoir positioned within the housing and coupled to an inflatable portion of a gastric band via the fluid inlet/outlet, the flexible reservoir containing a fluid and having an expanded configuration and a contracted configuration;
    a compression sheath positioned around a circumference of the flexible reservoir forming a cylinder, the compression sheath being movable to change a diameter of the cylinder;
    a driving mechanism positioned around the compression sheath, the driving mechanism configured to change the diameter of the cylinder to compress the flexible reservoir from the expanded configuration to the contracted configuration, thereby causing a portion of the fluid in the flexible reservoir to move to the inflatable portion of the gastric band; and
    a motor, coupled to the driving mechanism, the motor capable of actuating the driving mechanism.

2. The implantable system of claim 1 wherein the driving mechanism comprises a flexible screw.

3. The implantable system of claim 2 wherein an end of the flexible screw is attached to the housing.

4. The implantable system of claim 1 wherein the flexible reservoir is formed in a shape selected from a group consisting of a donut, a circle, an ellipse, a rectangle, and combinations thereof.

5. The implantable system of claim 1 further comprising a compressible structure positioned within the flexible reservoir for stabilizing boundaries of the flexible reservoir.

6. The implantable system of claim 1 wherein the motor is coupled to a sensing coil unit that communicates via radio frequency with an external controller for providing power and communications to the motor.

7. The implantable system of claim 1 further comprising a flow control device coupled to the fluid inlet/outlet for controlling movement of the fluid when filling the inflatable portion of the gastric band.

8. The implantable system of claim 7 wherein the flow control device is selected from a group consisting of a valve, a tube, a regulator, and combinations thereof.

9. The implantable system of claim 1 wherein the motor moves the driving mechanism by rotational movement or translational movement.

10. The implantable system of claim 1 further comprising a spring positioned around the compression sheath.

11. The implantable system of claim 10 wherein the spring is selected from a group consisting of an elastic spring, a polymer spring, a stretchable spring, a coplanar spring, a sheath spring, an enclosing spring, and combinations thereof.

12. The implantable system of claim 1 further comprising an access port coupled to the fluid inlet/outlet of the flexible reservoir for filling or draining the flexible reservoir or the inflatable portion of the gastric band.

* * * * *